United States Patent
Song et al.

(10) Patent No.: US 10,864,288 B2
(45) Date of Patent: Dec. 15, 2020

(54) DISINFECTING AND STERILIZING DEVICE FOR MEDICAL SENSOR

(71) Applicant: Healtech Med Inc., Hwaseong-si (KR)

(72) Inventors: Eun Seok Song, Seoul (KR); Ju Young Lee, Hwaseong-si (KR)

(73) Assignee: Healtech Med Inc., Hwaseong-si (KR)

( * ) Notice: Subject to any disclaimer, the term of this patent is extended or adjusted under 35 U.S.C. 154(b) by 0 days.

(21) Appl. No.: 16/314,447

(22) PCT Filed: Jun. 29, 2017

(86) PCT No.: PCT/KR2017/006902
§ 371 (c)(1),
(2) Date: Dec. 31, 2018

(87) PCT Pub. No.: WO2018/004274
PCT Pub. Date: Jan. 4, 2018

(65) Prior Publication Data
US 2019/0151485 A1    May 23, 2019

(30) Foreign Application Priority Data

Jun. 29, 2016  (KR) .......................... 10-2016-0081841

(51) Int. Cl.
*A61L 2/10*  (2006.01)
*A61C 19/00*  (2006.01)
(Continued)

(52) U.S. Cl.
CPC ................ *A61L 2/10* (2013.01); *A61C 19/00* (2013.01); *A61L 2/26* (2013.01); *A61B 6/145* (2013.01);
(Continued)

(58) Field of Classification Search
CPC .......... A61L 2/10; A61L 2202/12; A61L 2/26; A61C 19/00; A61C 19/02
See application file for complete search history.

(56) References Cited

U.S. PATENT DOCUMENTS 4,740,706 A * 4/1988 Murdock, III ............ A61L 2/10
250/455.11
8,016,483 B2 * 9/2011 Steward, Jr. ............ A61B 6/145
378/168
(Continued)

FOREIGN PATENT DOCUMENTS

KR   10-2005-0028739   3/2005
KR      10-0598417    7/2006
(Continued)

OTHER PUBLICATIONS

International Search Report and the Written Opinion dated Nov. 13, 2017 From the International Searching Authority Re. Application No. PCT/KR2017/006902 and Its Translation of Search Report Into English. (9 Pages).

*Primary Examiner* — Wyatt A Stoffa

(57) ABSTRACT

The present invention relates to a device capable of disinfecting and sterilizing a medical sensor by ultraviolet radiation, the device comprising: a box-shaped case having a space portion formed therein and having an opening formed through a surface thereof; a door hingedly coupled to a side of the case so as to open and close the opening of the case; a holding member installed in the space portion of the case and allowing a medical sensor to be held on a side thereof; and an ultraviolet sterilizer installed on a side of the holding member.

5 Claims, 8 Drawing Sheets

(51) Int. Cl.
  *A61L 2/26* (2006.01)
  *A61B 6/14* (2006.01)
(52) U.S. Cl.
  CPC ........ *A61L 2202/11* (2013.01); *A61L 2202/24* (2013.01)

(56) References Cited

U.S. PATENT DOCUMENTS

| | | | | |
|---|---|---|---|---|
| 9,107,973 | B1* | 8/2015 | Robinson | A61L 2/22 |
| 9,186,475 | B2* | 11/2015 | Arcilla | A61M 16/06 |
| 9,314,215 | B2* | 4/2016 | Abramovich | A61B 6/4435 |
| 9,339,570 | B2* | 5/2016 | Whitney | A61L 2/10 |
| 9,433,694 | B1* | 9/2016 | Hsu | A46B 17/065 |
| 9,802,019 | B2* | 10/2017 | Arcilla | A61M 16/06 |
| 2001/0055368 | A1* | 12/2001 | Carroll | H04N 5/367 |
| | | | | 378/189 |
| 2003/0034459 | A1* | 2/2003 | Bonin | A61L 2/06 |
| | | | | 250/491.1 |
| 2011/0051900 | A1* | 3/2011 | Steward, Jr. | A61B 6/4435 |
| | | | | 378/147 |
| 2015/0217010 | A1* | 8/2015 | Whitney | A61L 2/10 |
| | | | | 250/455.11 |
| 2016/0008499 | A1* | 1/2016 | Sunkara | A61L 2/24 |
| | | | | 422/24 |
| 2016/0074546 | A1* | 3/2016 | Rizzone | A61L 2/26 |
| | | | | 250/455.11 |
| 2017/0086760 | A1* | 3/2017 | Kim | A61C 9/004 |
| 2017/0224858 | A1* | 8/2017 | Stibich | A61L 2/16 |
| 2017/0333618 | A1* | 11/2017 | Krohn | A61M 5/001 |
| 2018/0078330 | A1* | 3/2018 | Russ | A61B 90/70 |
| 2018/0339076 | A1* | 11/2018 | Stibich | A61L 2/26 |
| 2019/0060494 | A1* | 2/2019 | Mauzerall | A61B 50/33 |

FOREIGN PATENT DOCUMENTS

| | | |
|---|---|---|
| KR | 10-2011-0063702 | 6/2011 |
| KR | 20-2013-0000320 | 1/2013 |
| KR | 10-2016-0039650 | 3/2016 |
| KR | 10-1665601 | 10/2016 |
| WO | WO 2018/004274 | 1/2018 |

* cited by examiner

DISINFECTING AND STERILIZING DEVICE FOR MEDICAL SENSOR

RELATED APPLICATIONS

This application is a National Phase of PCT Patent Application No. PCT/KR2017/006902 having International filing date of Jun. 29, 2017, which claims the benefit of priority of Korean Patent Application No. 10-2016-0081841 filed on Jun. 29, 2016. The contents of the above applications are all incorporated by reference as if fully set forth herein in their entirety.

FIELD AND BACKGROUND OF THE INVENTION

The present invention relates to a disinfecting and sterilizing device and more specifically, to a disinfecting and sterilizing device for a medical sensor by means of ultraviolet radiation.

For instance, at a dental clinic etc., a medical sensor (intraoral sensor) is directly inserted into the mouth of a subject, and force is applied, such that the medical sensor closely contacts the inside of the oral cavity of the subject, when a dental X-ray is taken. Due to this, a hole can be made in the wrap covering the medical sensor, and the medical sensor can be directly contaminated by saliva or blood.

A cross infection can occur when such a medical sensor is contaminated by saliva or blood. Thus, before being used for a subject, a medical sensor is generally disinfected with alcohol and wrapped in disposable wrap consisting of hygiene vinyl. Then a dental X-ray is taken in order for information on the oral cavity of the subject to be obtained.

However, conventionally, there are cases in which a medical sensor is kept with its wrap removed after an X-ray is taken. While the medical sensor is kept with its wrap removed, it is exposed to various bacteria and impurities. Thus, the medical sensor is kept in unhygienic conditions. Although the medical sensor is disinfected with alcohol etc. it is difficult to confirm whether the medical sensor is completely sterilized. Additionally, when the medical sensor is wrapped after sterilization, there is a possibility that the medical sensor is contaminated again. Thus, there is a potential risk that a cross infection may occur. This makes subjects worried.

Additionally, in the case in which a practitioner disinfects a medical sensor and wraps the same firsthand, the procedures of disinfecting and sterilizing a medical sensor are too cumbersome for the practitioner to carry out each time an X-ray is taken. Thus, this negatively affects efficiency in examinations.

Additionally, it is cumbersome to disinfect a medical sensor with alcohol etc. whenever the medical sensor is used. Further, there are cases where a conventional sterilizer that is a costly sensor cannot be used due to its failure or damage etc. When a medical sensor is covered with hygienic vinyl and used without being disinfected, a cross infection is highly likely to occur.

SUMMARY OF THE INVENTION

As a means to solve the above-described problems, the present invention is directed to providing a disinfecting and sterilizing device for a medical sensor, which is capable of preventing a cross infection when a medical sensor is used.

The present invention is also directed to providing a disinfecting and sterilizing device for a medical sensor, which enables a medical sensor to be held always and to be disinfected and sterilized.

The present invention is also directed to providing a disinfecting and sterilizing device for a medical sensor, which is capable of disinfecting and sterilizing wrap together with a medical sensor when disinfecting and sterilizing the medical sensor.

The present invention is also directed to providing a disinfecting and sterilizing device for a medical sensor, which is capable of disinfecting and sterilizing a cable through minimized contact between a cable of a medical sensor and a holding member.

As a means to achieve the above-described purposes, a disinfecting and sterilizing device for a medical sensor includes: a box-shaped case having a space portion formed therein and having an opening formed through a surface thereof; a door hinge-coupled to one side of the case so as to open and close the opening of the case; a holding member installed in the space portion of the case and allowing a medical sensor to be held on one side thereof; and an ultraviolet sterilizer installed on one side of the holding member.

According to one feature of the present invention, the holding member may include a coupling part coupled to one surface of the case opposing the opening, an extension part extending from one side of the coupling part toward the opening, a support part bent and extending from an end of the extension part, and a prop part protruding from an end of the support part so as to support one side of the medical sensor.

According to another feature of the present invention, the support part may include a first support part bent and extending from the end of the extension part and a second support part inclined at a predetermined angle and extending from an end of the first support part.

According to another feature of the present invention, the holding member may further include a guide hole cut from one side of the extension part to one side of the support part.

According to another feature of the present invention, the prop part may include a pair of prop members spaced apart from each other and protruding from one side of the second support part, and a cable of the medical sensor may pass a space between the pair of prop members and the guide hole and extend outward.

According to another feature of the present invention, the holding member may include a coupling part coupled to a bottom surface of the case, a support part bent and extending from an end of the coupling part in the direction of the opening of the coupling part, and a prop part protruding from the end of the support part so as to support one side of the medical sensor.

According to another feature of the present invention, the holding member may include a support part one end of which is coupled to the bottom surface of the case and the other end of which extends upward, and a prop part protruding from the end of the support part so as to support one side of the medical sensor.

According to another feature of the present invention, the ultraviolet sterilizer may include a housing provided on one side of the space portion of the case, and an ultraviolet lamp installed on one side of the housing.

According to yet another feature of the present invention, a disinfecting and sterilizing device for a medical sensor may further include a wrap hanging part installed on another side of the holding member so as to hang and hold wrap.

According to a disinfecting and sterilizing device for a medical sensor of the present invention, a cross infection caused by the repetitive use of a medical sensor may be prevented.

Additionally, according to a disinfecting and sterilizing device for a medical sensor of the present invention, wrap together with a medical sensor may be disinfected and sterilized.

Additionally, according to a disinfecting and sterilizing device for a medical sensor of the present invention, a cable of a medical sensor may be disinfected and sterilized through minimized contact between a cable of a medical sensor and a holding member.

Additionally, according to a disinfecting and sterilizing device for a medical sensor of the present invention, a costly sensor may be prevented from being broken because the medical sensor is stably held and sterilized.

DESCRIPTION OF SPECIFIC

Embodiments of the Invention

Figure 1:
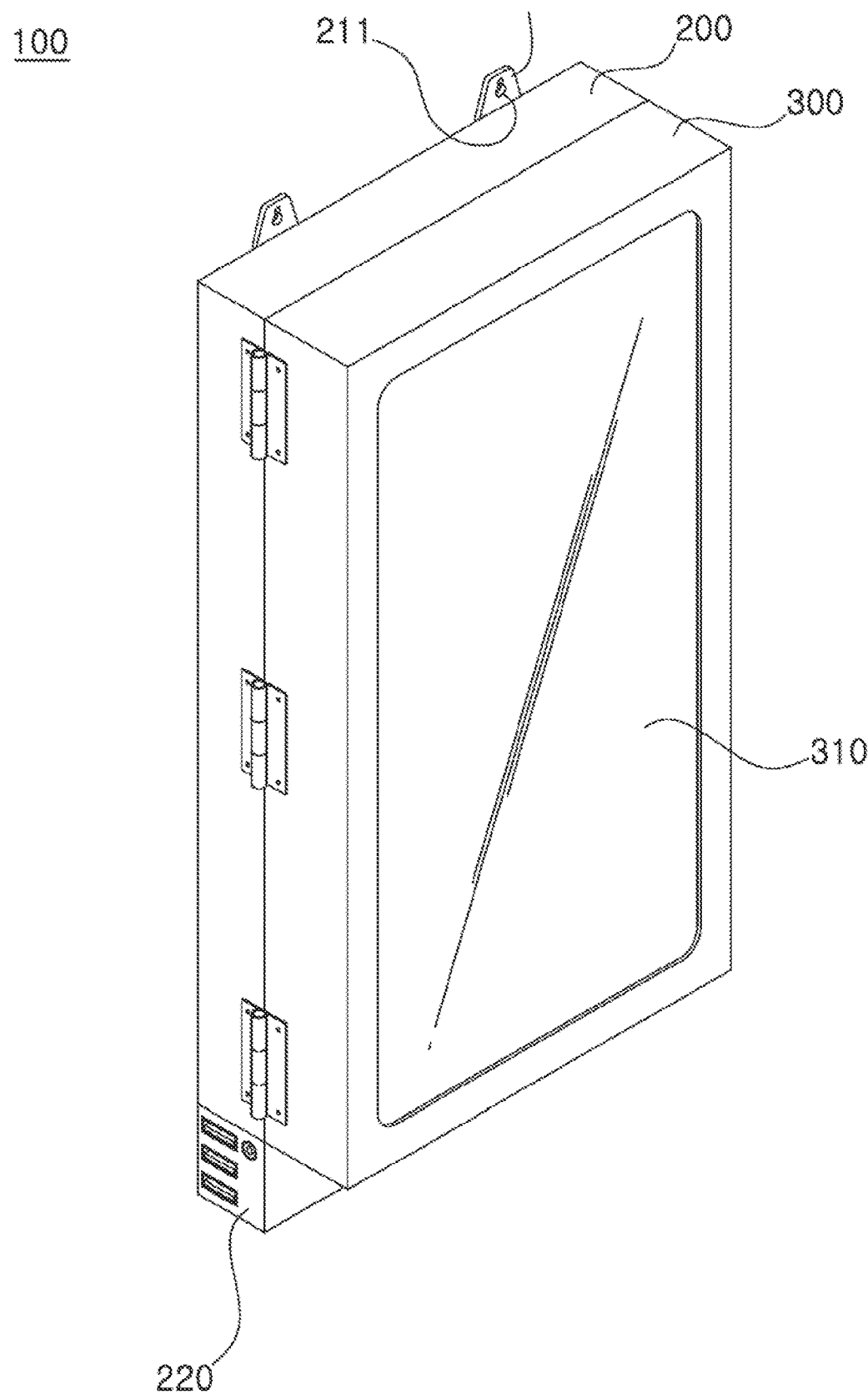
FIGS. 1 and 2 are perspective views of a disinfecting and sterilizing device for a medical sensor according to an embodiment of the present invention.

Embodiments of the present invention will be specifically described with reference to the attached drawings. However, the below-described embodiments are provided such that one having ordinary skill in the art to which the present invention pertains may easily embody the present invention. Thus, it should be understood that the present invention is not construed as being limited to the embodiments. Further, in describing various embodiments of the present invention, like reference numerals denote elements having identical technical features.

Figure 2:
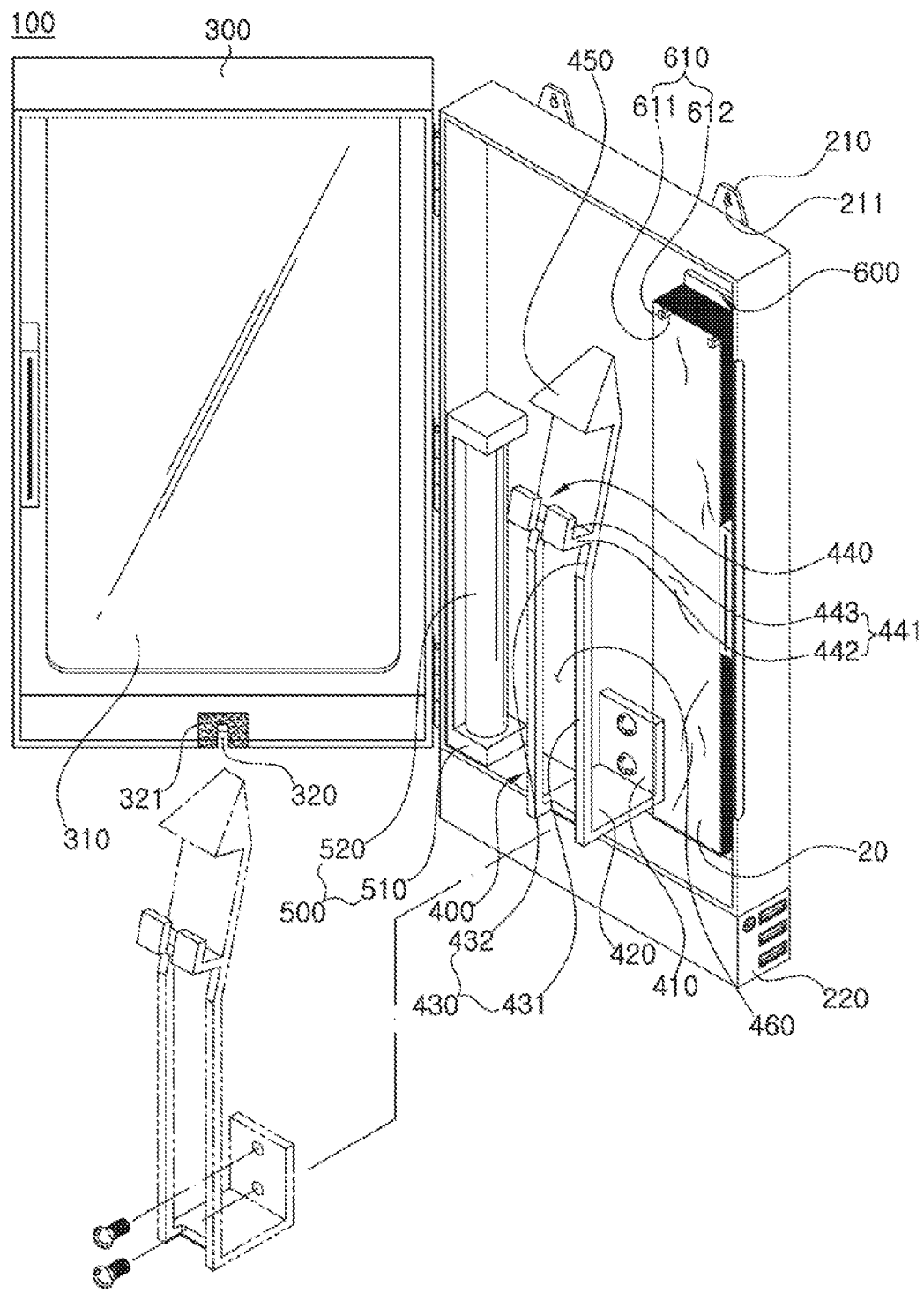
Figure 3:
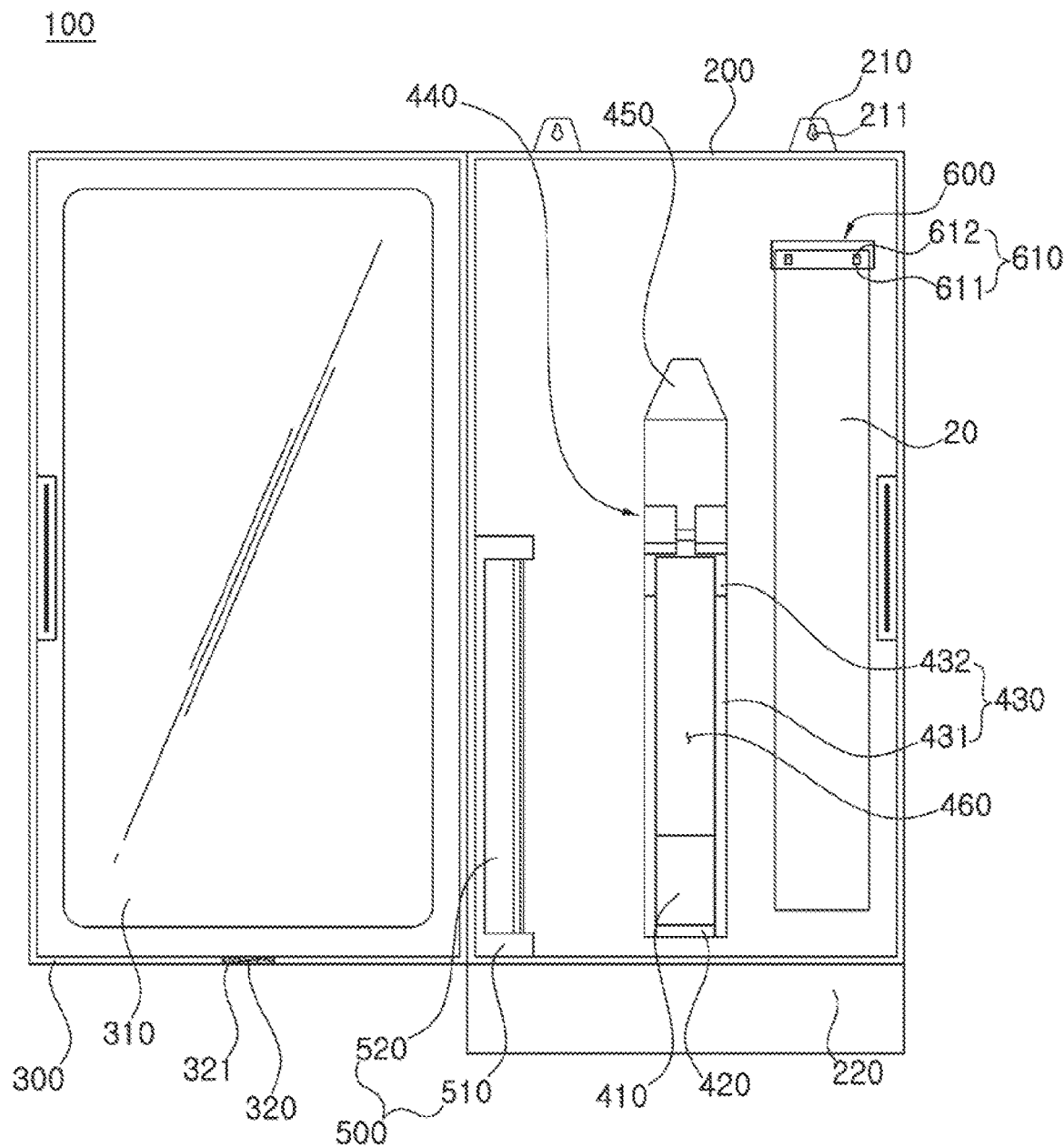
FIG. 3 is a front view of a disinfecting and sterilizing device for a medical sensor according to an embodiment of the present invention.

FIGS. 1 and 2 are perspective views of a disinfecting and sterilizing device for a medical sensor according to an embodiment of the present invention, and FIG. 3 is a front view of a disinfecting and sterilizing device for a medical sensor according to an embodiment of the present invention.

As illustrated in FIGS. 1 to 3, a disinfecting and sterilizing device for a medical sensor 100 according to an embodiment of the present invention includes a box-shaped case 200, a door 300 for opening and closing the case 200, a holding member 400 installed in the case 200 and supporting a medical sensor 10 and an ultraviolet sterilizer 500 for disinfecting and sterilizing the medical sensor 10 by means of ultraviolet radiation.

Herein, the case 200 preferably consists of a wooden material, a metallic material or a synthetic resin, has a hexahedron shape with a space portion formed therein and an opening formed at a front surface thereof and includes a hanging part 210 having a through hole 211 and protruding from an upper end of a rear surface thereof so that a disinfecting and sterilizing device may be hung on the wall.

Additionally, the case 200 may have a terminal part 220, provided with a power port or a USB port for access to power or a PC, on one side of a lower end thereof.

For instance, three USB ports may be provided. When a medical sensor 10 has to be connected with a PC, one USB port may be connected with a cable of a medical sensor 10 while another USB port may be connected with a USB cable connected with a USB port of the PC. Additionally, as described below with reference to FIG. 8, when a plurality of disinfecting and sterilizing devices for a medical sensor 100, installed in parallel with each other, are used, the other USB port may be used to connect these devices in parallel by means of a USB cable. Herein, the number of USB ports may vary according to the needs.

The door 300, preferably, has a box shape with an opened rear and consists of a material the same as that of the case 200. The door is hinge-coupled to one side of the front surface of the case 200 so as to open and close the opening of the case 200. Additionally, a window 310 consisting of a transparent material may be installed at the front surface of the door 300 such that the inside of the case may be checked with the naked eye. Preferably, the inner surface of the window 310 is coated with an ultraviolet reflective film or an ultraviolet reflective material.

The holding member 400 is provided inside the case 200 for holding a medical sensor 10 to be disinfected and sterilized. The holding member 400 is configured to minimize contact between the medical sensor 10 and the case 200 so as to prevent the medical sensor 10 from being contaminated by impurities. As an example, one end of the holding member 400 may be coupled to the rear surface of the inner side of the case 200 while the other end of the holding member may be spaced forward apart from the rear surface and may extend in parallel with the rear surface. As another example, one end of the holding member 400 may be coupled to the lower surface of the inner side of the case 200 while the other end of the holding member may extend from the lower surface in parallel with the rear surface.

The holding member 400 may consist of a wooden material or a synthetic resin and preferably, may consist of a metallic material such as stainless steel (SUS) or aluminum etc. that is light and resistant to rust.

As illustrated in the drawings, the holding member 400 according to an embodiment of the present invention may include a coupling part 410 coupled to the rear surface of the case 200, an extension part 420 perpendicularly extending forward from one side of the coupling part 410, a support part 430 perpendicularly bent and extending from the end of the extension part 420, and a prop part 440 protruding from the end of the support part 430 and supporting the medical sensor 10.

Herein, the coupling part 410 has a plate shape, is welded, attached or fused to the rear surface of the case 200, or, as illustrated in FIG. 2, is detachably coupled to the rear surface of the case by means of a bolt coupling etc. and supports the extension part 420 and the support part 430.

The extension part 420 extends from one side of the coupling part 410 toward the opening (forward). For instance, the extension part may have a plate shape with a predetermined width and length. The extension part 420 may be integrally formed with the coupling part 410, or a separate member may be coupled to the coupling part 410 so as to form an extension part 420. An angle formed by the coupling part 410 and the extension part 420 may be properly selected according to a standard such as the depth of the case 200 etc. In this embodiment, the extension part 420 perpendicularly extends from one side of the coupling part 410.

The support part 430 is bent and extends from the end of the extension part 420 in one direction (toward the ceiling of the case 200 in the drawings). In this case, an angle formed by the extension part 420 and the support part 430 may be properly selected according to a standard such as the depth of the case 200, the length of the support part 430 etc. In this embodiment, the support part 430 perpendicularly extends from the end of the extension part 420.

The prop part 440 including a pair of prop members 441 protrudes from the front surface of the end of the support part 430 so as to support one side (lower end) of the medical sensor 10. As an example, the prop member 441 may include a first mounting part 442 protruding forward from the front surface of the support part 430 and supporting the lower end of the medical sensor 10, and a first catching part 443 protruding upward from the end of the first mounting part 442 and preventing the medical sensor 10 from escaping forward. The pair of prop members 441 are spaced apart from each other in parallel with each other in the widthwise direction of the support part 430.

Herein, preferably, the end of the support part 430 is inclined backward at a predetermined angle such that the medical sensor 10 mounted onto the prop part 440 may be stably supported. According to an embodiment of the present invention, the support part 430 includes a first support part 431 perpendicularly bent and extending from the end of the extension part 420 and a second support part 432 inclined at a predetermined angle backward and extending from the end of the first support part 431. The above-described prop part 440 protrudes from the front surface of the second support part 432 that is inclined. In this case, the lower end of the medical sensor 10 is mounted onto the prop part 440 in the state where the medical sensor is inclined backward while the rear surface of the medical sensor is stably supported by the second support part 432.

Additionally, a guide part 450, which has a tapered shape such that the guide part becomes thinner toward the end thereof and protrudes from the front surface of the second support part 432, is formed at the upper side of the prop part 440. This is to easily open and close the inlet of the below-described wrap 20 when the wrap 20 covers the medical sensor 10 having been mounted onto the prop part 440.

As another example of the present invention, the coupling part 410 of the holding member 400 may be coupled to the lower surface of the case 200. In such an embodiment, the extension part 420 is omitted, and the support part 430 is directly coupled to the coupling part 410, such that the support part 430 extends in parallel with the rear surface of the coupling part.

Meanwhile, a cable 11 extends from one side (e.g., lower end) of the medical sensor 10 for connecting with external power or a PC. According to an embodiment of the present invention, the cable 11 may also be disinfected and sterilized.

The cable 11 of the medical sensor 10 extends from one side of the medical sensor 10, extends through the space between the pair of prop members 441 and extends downward along the support part 430. In this case, contact between the cable 11 and the support part 430 has to be minimized so as to improve efficiency of disinfecting and sterilizing the cable 11. To this end, a guide hole 460, cut and having a predetermined width and length, is formed at the support part 430 and the extension part 420.

Herein, the guide hole 460 extends from one side of the extension part 420 through the first support part 431 to one side of the second support part 432, more specifically, to one position of the lower end of the prop part 440. In this case, the cable 11 passes the space between the pair of prop members 441 and the guide hole 460 and extends downward by means of the self-weight thereof.

Additionally, a through hole 320 is formed at the bottom surface of the door 300 (the opposing surface of the door 300 adjacent to the extension part 420 when the door 300 and the case are coupled) so as to oppose the guide hole 460 of the extension part 420, and the cable 11 extends outward through the through hole 320. In this case, the through hole 320 preferably is coupled to a packing 321 consisting of a soft material such as rubber or silicone etc. so as to prevent the cable 11 from flowing and prevent foreign substances from being introduced through the through hole 320. As another example, when the door 300 has a plate shape, the through hole 320 and the packing 321 may be formed on the bottom surface of the case 200.

An ultraviolet sterilizer 500 is installed on one side of the space portion of the case 200 so as to disinfect and sterilize the medical sensor 10. The ultraviolet sterilizer 500 may include a housing 510 installed on one side of the holding member 400, and an ultraviolet lamp 520 which is provided on one side of the housing 510 and radiates ultraviolet rays into the space portion when power is supplied.

In this case, a reflective part (invisible) for reflecting ultraviolet rays is preferably formed on one side of the housing 510 surrounding the ultraviolet lamp 520 so as to improve the efficiency of the ultraviolet lamp 520, and the inner surface of the case 200 is preferably provided with a material with high reflectivity etc. so as to improve the effect of reflecting ultraviolet rays.

A wrap hanging part 600 protrudes from the upper side of the rear surface of the case 200 so as to hang pocket-shaped wrap 20 for wrapping the medical sensor 10 and to disinfect and sterilize the same. However, this is nothing but an embodiment of the present invention. The position of the wrap hanging part 600 may be freely selected according to the needs as long as the wrap 20 hung on the wrap hanging part 600 is stored in a space divided by the case 200 and the door 300 when the door 300 is closed. For instance, the wrap hanging part 600 may be formed on the rear surface or the ceiling of the door 300, on the lateral surface or the ceiling of the case 200.

In this embodiment, the wrap hanging part 600 includes a pair of hanging members 610 which are formed at the rear surface of the case 200 and spaced apart from each other. In this case, each of the hanging members 610 may include a second mounting part 611 protruding forward from the rear surface of the case 200, and a second catching part 612 bent upward at the end of the second mounting part 611.

The wrap 20 consists of hygiene vinyl, and one or more sheets of wrap 20 may be hung on and stored in the wrap hanging part 600. When the ultraviolet sterilizer 500 operates, the wrap hung on the wrap hanging part 600 is disinfected and sterilized together with the medical sensor 10.

Figure 4:
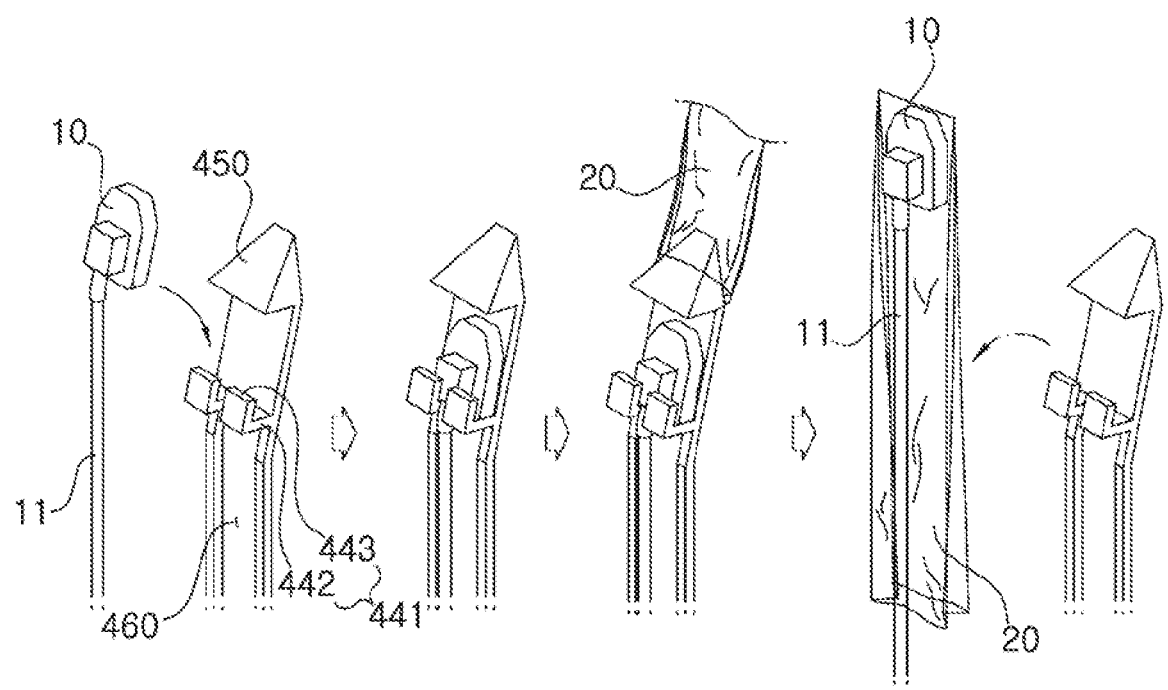
FIGS. 4 and 5 are views illustrating a state where a medical sensor is being covered with wrap.
Figure 5:
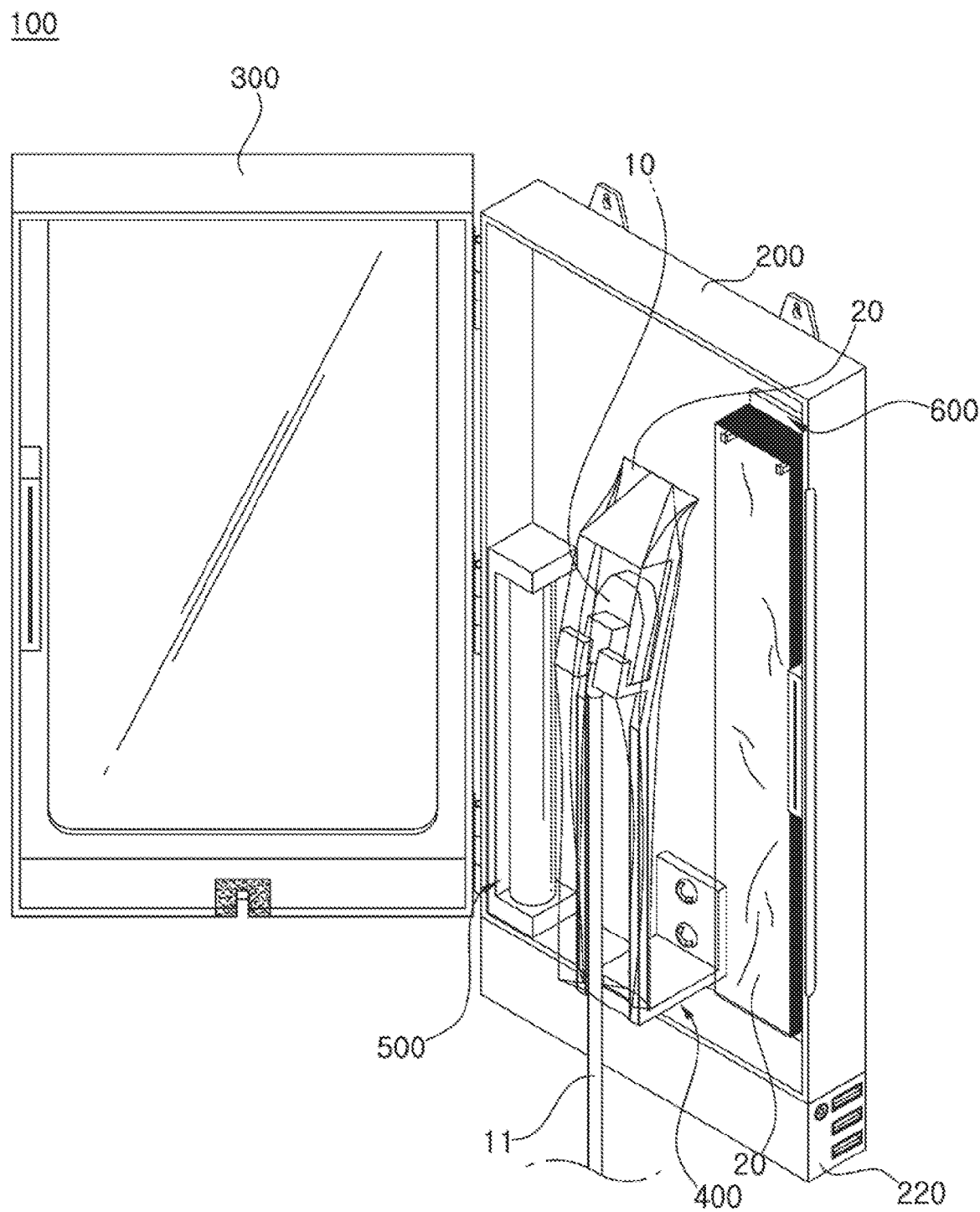

FIG. 4 is a view illustrating a state where a medical sensor is being covered with wrap, and FIG. 5 is a view illustrating a state where a medical sensor is covered with wrap.

In the case in which a medical sensor 10 is used after the medical sensor 10 is disinfected and sterilized by the ultraviolet sterilizer 500, wrap 20 is withdrawn from the wrap hanging part 600, and a medical sensor 10, as illustrated in FIG. 4, is covered with the wrap 20 and then used. In this case, the wrap 20 prevents the medical sensor 10 from being contaminated by the body fluids of a patent or by foreign substances.

Figure 6:
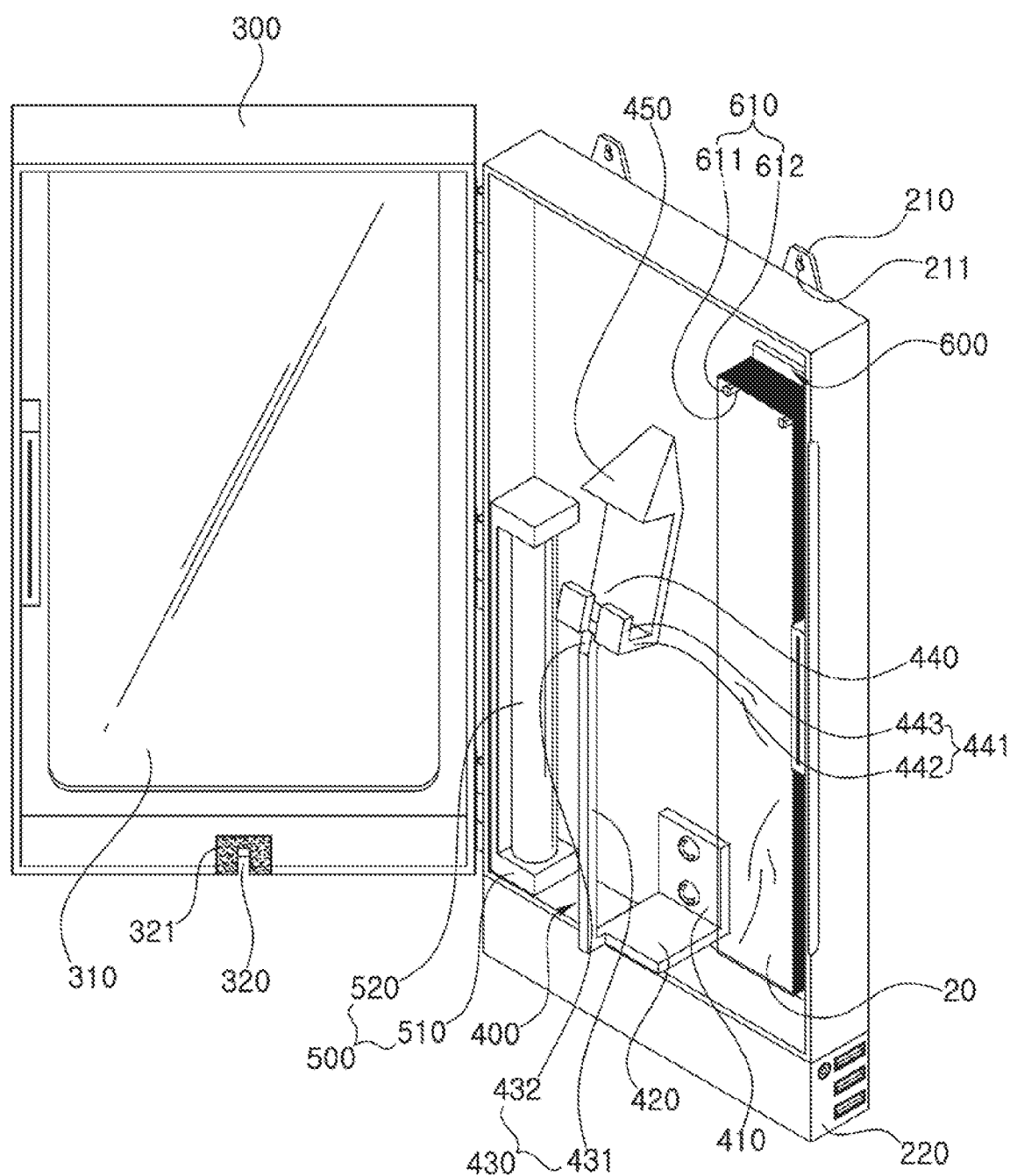
FIG. 6 is a perspective view of a disinfecting and sterilizing device for a medical sensor according to another embodiment of the present invention.

FIG. 6 is a perspective view of a disinfecting and sterilizing device for a medical sensor according to another embodiment of the present invention.

According to the embodiment that has been described with reference to FIGS. 1 to 3, the guide hole 460 are formed at the support part 430 to prevent the cable 11 from contacting the holding member 400. However, according to another embodiment of the present invention, the extension part 420 and the support part 430, as illustrated in FIG. 5, may be configured to extend disproportionately toward one side (left side in the drawing) of the prop part 440.

In this case, the cable 11 extending from the medical sensor 10 is spaced and extends from one side (right side in the drawing) of the support part 430. Thus, the cable 11 is prevented from contacting the support part 430. Even in this case, the guide hole 460 is preferably formed at an area of the extension part 420, where the cable 11 passes, so as to prevent the cable 11 from contacting the extension part 420.

Figure 7:
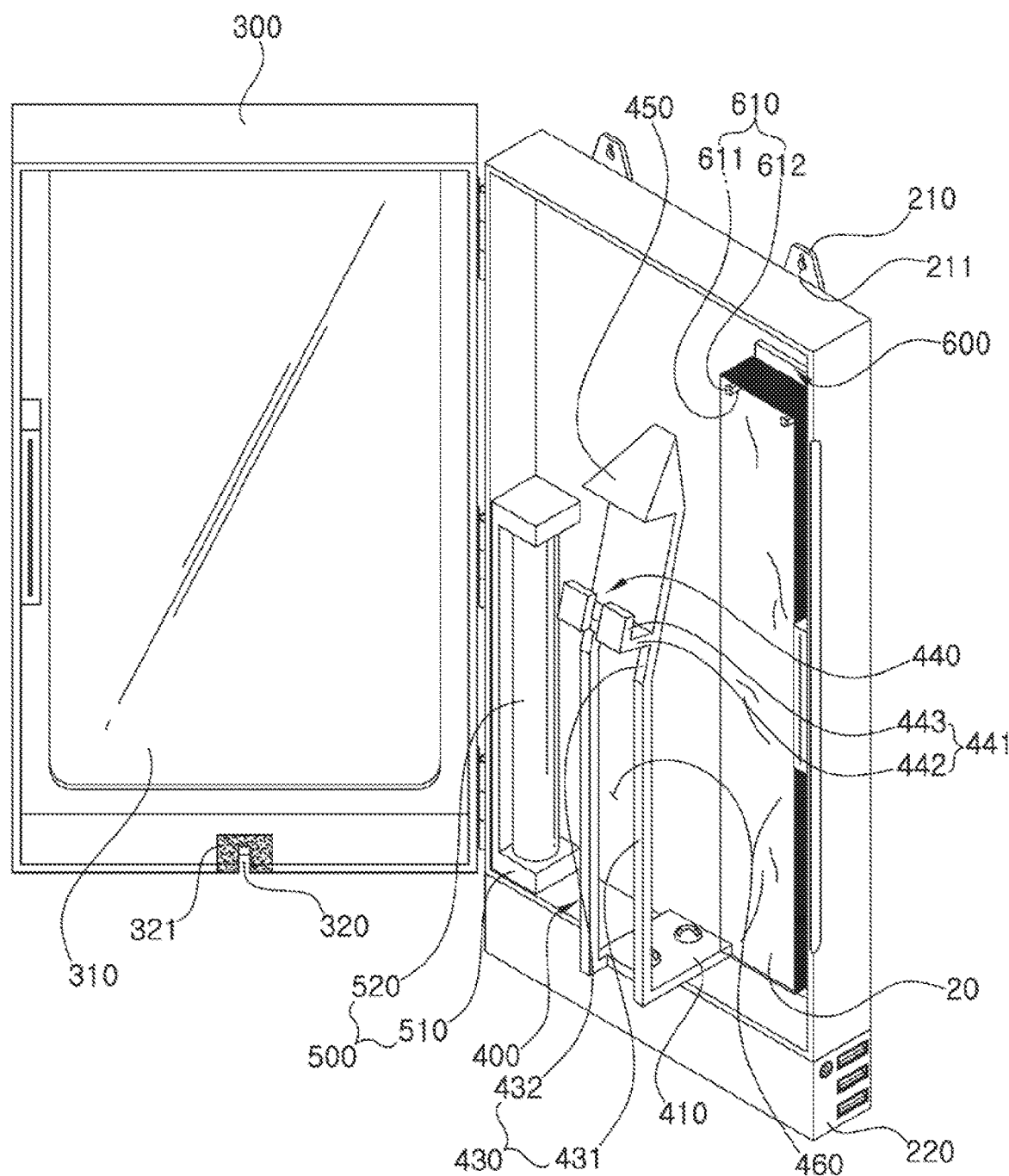
FIG. 7 is a perspective view of a disinfecting and sterilizing device for a medical sensor according to another embodiment of the present invention.

FIG. 7 is a perspective view of a disinfecting and sterilizing device for a medical sensor according to another embodiment of the present invention. According to FIG. 7, the coupling part 410 is coupled to the bottom surface of the case 200, and the support part 430 is bent upward and extends from the front end of the coupling part 410, i.e. the end of the coupling part 410 in the direction of the opening of the coupling part without a separate extension part 420. As a modified example, one end of the support part 430 may be directly coupled to the bottom surface of the case 200, and the other end of the support part may extend upward without a separate coupling part 410 or a separate extension part 420.

Figure 8:
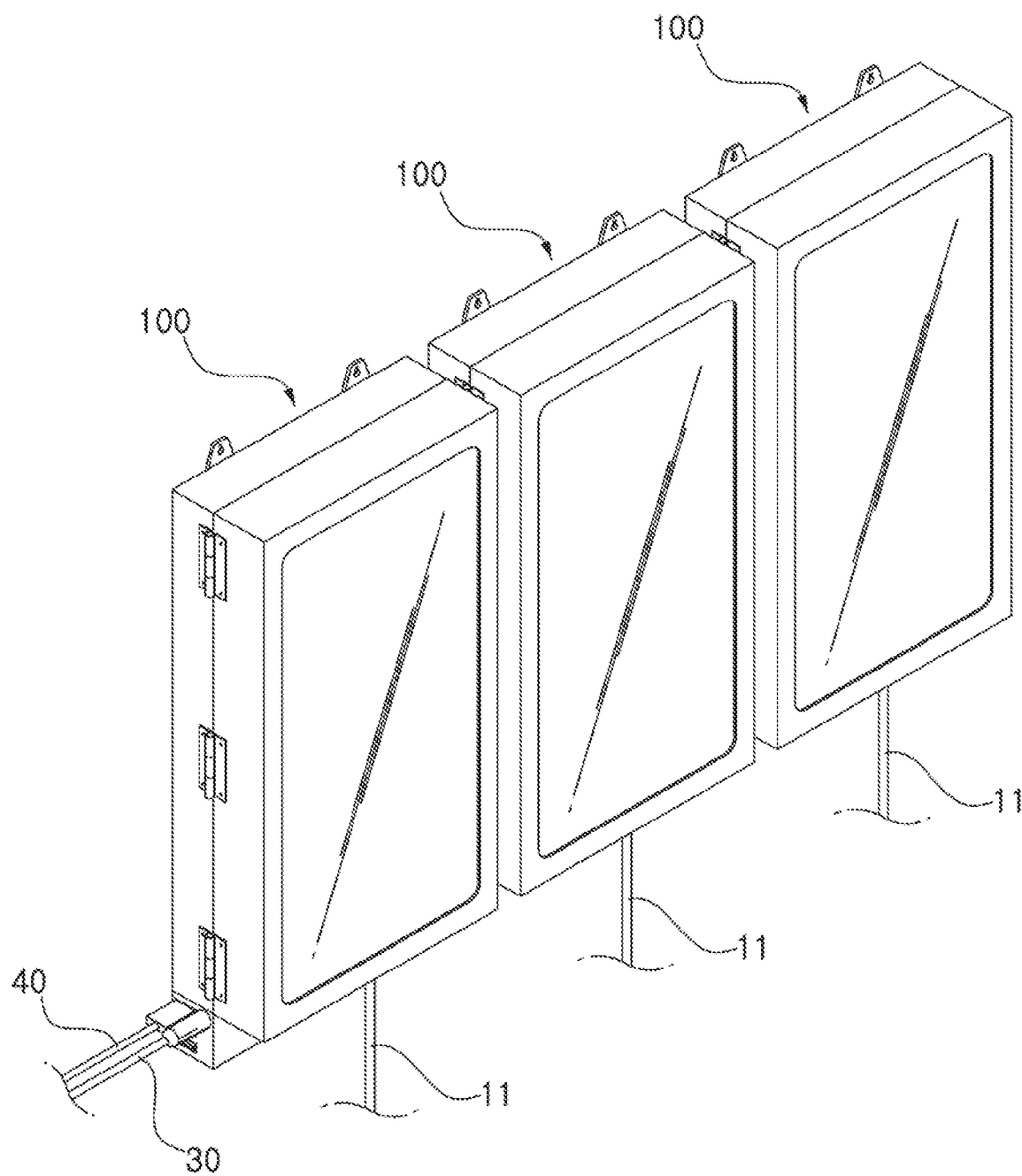
FIG. 8 is a perspective view of a disinfecting and sterilizing device for a medical sensor according to yet another embodiment of the present invention.

FIG. 8 is a perspective view of a disinfecting and sterilizing device for a medical sensor according to yet another embodiment of the present invention.

According to yet another embodiment of the present invention, a plurality of disinfecting and sterilizing devices for a medical sensor 100, as illustrated in the drawing, may be installed in parallel with each other. In this case, each of the disinfecting and sterilizing devices for a medical sensor 100 may be provided with a power port and a USB port respectively at both sides of the terminal part 220 and may be electrically connected in parallel with each other. A user may connect a power cable 30 and a USB cable 40 to the terminal part 220 of the leftmost or rightmost disinfecting and sterilizing device for a medical sensor 100 so as to supply power to the plurality of disinfecting and sterilizing devices for a medical sensor 100 collectively or to receive data from the plurality of disinfecting and sterilizing devices for a medical sensor 100.

The embodiments of the present invention have been described. However, it should be understood that the present invention may be modified in many different forms by one having ordinary skill in the art to which the present invention pertains within the scope of the claims of the present invention.

INDUSTRIAL APPLICABILITY

According to a disinfecting and sterilizing device for a medical sensor of the present invention, a medical sensor may be disinfected and sterilized without concern over a cross infection.

Additionally, according to a disinfecting and sterilizing device for a medical sensor of the present invention, wrap and a cable together with a medical sensor may be disinfected and sterilized.

Additionally, according to a disinfecting and sterilizing device for a medical sensor of the present invention, a costly sensor may be prevented from being broken during the disinfection and sterilization processes.

What is claimed is:

1. A disinfecting and sterilizing device for a medical sensor comprising:
   a box-shaped case having a space portion formed therein and having an opening formed through a surface thereof;
   a door hinge-coupled to one side of the case so as to open and close the opening of the case;
   a holding member installed in the space portion of the case and allowing a medical sensor to be held on one side thereof; and
   an ultraviolet sterilizer installed on one side of the holding member,
   wherein the holding member comprises a coupling part coupled to one surface of the case opposing the opening, an extension part extending from one side of the coupling part toward the opening, a support part bent and extending from an end of the extension part, a prop part protruding from an end of the support part so as to support one side of the medical sensor, and a guide hole cut from one side of the extension part to one side of the support part,
   wherein the support part comprises a first support part bent and extending from the end of the extension part and a second support part inclined at a predetermined angle and extending from an end of the first support part, and
   wherein a guide part, which has a tapered shape such that the guide part becomes thinner toward an end thereof and protrudes from a front surface of the second support part, is formed at an upper side of the prop part,
   wherein the prop part comprises a pair of prop members spaced apart from each other and protruding from one side of the second support part,
   wherein the pair of prop members include a first mounting part protruding forward from a front surface of the support part and supporting a lower end of the medical sensor, and a first catching part protruding upward from an end of the first mounting part and preventing the medical sensor from escaping forward,
   wherein the pair of prop members are spaced apart from each other in parallel with each other in a widthwise direction of the support part,
   wherein a wrap hanging part protrudes from an upper side of an rear surface of the case so as to hang pocket-shaped wrap for wrapping the medical sensor and to disinfect and sterilize the medical sensor.

2. The disinfecting and sterilizing device for a medical sensor according to claim 1, wherein a cable of the medical sensor passes a space between the pair of prop members and the guide hole and extends outward.

3. The disinfecting and sterilizing device for a medical sensor according to claim 1, wherein the coupling part is coupled to a bottom surface of the case and the support part is bent and extending from an end of the coupling part in a direction of the opening of the case.

4. The disinfecting and sterilizing device for a medical sensor according to claim 1, wherein one of the first and second support parts is coupled to a bottom surface of the case and the other extends upward.

5. The disinfecting and sterilizing device for a medical sensor according to claim 1, wherein the ultraviolet sterilizer comprises a housing provided on one side of the space portion of the case, and an ultraviolet lamp installed on one side of the housing.

* * * * *